(12) United States Patent  
Jacques et al.

(10) Patent No.: US 8,735,594 B2  
(45) Date of Patent: May 27, 2014

(54) FUNCTIONALIZED SUBSTRATE AND USES THEREOF

(75) Inventors: Pierre-Andre Jacques, Sainte Consorce (FR); Vincent Artero, Quaix-en-Chartreuse (FR); Marc Fontecave, Saint Ismier (FR); Adeline Leyris, Plats (FR); Muriel Matheron, Chambery (FR)

(73) Assignee: Commissariat a l'Energie Atomique et Aux Energies Alternatives, Paris (FR)

( * ) Notice: Subject to any disclaimer, the term of this patent is extended or adjusted under 35 U.S.C. 154(b) by 174 days.

(21) Appl. No.: 13/090,613

(22) Filed: Apr. 20, 2011

(65) Prior Publication Data

US 2011/0257406 A1      Oct. 20, 2011

(30) Foreign Application Priority Data

Apr. 20, 2010 (FR) ...................... 10 53019

(51) Int. Cl.
*C07F 15/04* (2006.01)
*C07F 15/06* (2006.01)
*C07D 249/04* (2006.01)
*C07D 249/16* (2006.01)
*C07C 247/04* (2006.01)
*C07C 259/04* (2006.01)

(52) U.S. Cl.
CPC ............. *C07F 15/045* (2013.01); *C07F 15/065* (2013.01); *C07D 249/04* (2013.01); *C07D 249/16* (2013.01); *C07C 247/04* (2013.01); *C07C 259/04* (2013.01)
USPC ............... 548/104; 548/108; 552/11; 564/12; 564/268

(58) Field of Classification Search
CPC ... C07F 15/045; C07F 15/065; C07D 249/04; C07D 249/16; C07C 247/04; C07C 259/04
USPC ................ 548/104, 108; 552/11; 564/12, 268
See application file for complete search history.

(56) References Cited

U.S. PATENT DOCUMENTS 3,584,022 A      6/1971 Costa et al.

OTHER PUBLICATIONS

Fontecave, Marc et al., "Bioinspired catalysis at the crossroads between biology and chemistry: A remarkable example of an electrocatalytic material mimicking hydrogenases," Compte Rendus Chimie (2010).
Jacques, Pierre-Andre et al., "Cobalt and nickel diimine-dioxime complexes as molecular electrocatalysts for hydrogen evolution with low overvoltages," PNAS (2009), vol. 106, pp. 20627-20632.
French Search Report dated Dec. 13, 2010.

*Primary Examiner* — Joseph Kosak
(74) *Attorney, Agent, or Firm* — Scully, Scott, Murphy & Presser, P.C.

(57) ABSTRACT

The present invention is directed towards proposing ligands of formula:

-continued (III)

and is also directed towards a substrate at the surface of which is immobilized at least one unit of formula:

(I)

23 Claims, 4 Drawing Sheets

FUNCTIONALIZED SUBSTRATE AND USES THEREOF

The present invention relates to novel ligands and catalytic complexes and also to substrates functionalized with such species.

BACKGROUND

Metal complexes are well known for their chemical or physicochemical properties and are exploited in this respect in many industrial fields including, for example, the fields of catalysis, magnetism, molecular electronics, luminescence, the environment, imaging and therapeutics.

In general, these complexes involve one or more metals coordinated with one or more ligands.

Among the potential ligands, tetradentate ligands of diimine-dioxime type are particularly appreciated due to their ability to form stable complexes with transition metals such as rhodium (Rh), iron (Fe), silver (Ag), copper (Cu), nickel (Ni) or cobalt (Co) (cf. Collman, J. P., Brauman, J. I., Madonik, A. M., *Organometallics*, 1986, 5, 310-322, Anderson, O. P., Perkins, C., Brito, K., *Inorg. Chem.* 1983, 22, 1267-1273, Eltayeb, M. A., Sulfab, Y., *Polyhedron*, 2007, 26, 39-42, Stynes, Dennis V.; Singh, Kowsill; Ng, Betty; Wilshire, Susan; *Inorg, Chim. Acta*; Vol. 58; 1982, 58, 179-186). In general, a diimine-dioxime ligand coordinates the metal atoms by adopting a planar or quasi-planar conformation. It is then said to coordinate the metal in an equatorial plane. Other coordination positions are then left vacant, and are termed "axial coordination positions".

In particular, it is known practice to use certain diimine-dioxime complexes as catalysts for polymerization reactions of methyl methacrylate (cf. Zangrando, E.; Trani, M.; Stabon, E.; Carfagna, C.; Milani, B.; Mestroni, G. *Eur. J. Inorg. Chem.* 2003, 2683-2692) or for electroproduction of hydrogen (cf. Jacques. P.-A.; Artero, V.; Pécaut, J.; Fontecave, M.; *Proc. Natl. Acad. Sci. USA*. 2009, 116, 20627-20632).

Such complexes may also be used in imaging, in which a $^{64}$Cu diimine-dioxime complex has been envisaged as a radiopharmaceutical compound for positron emission tomography (cf. Kiani, S.; Staples, R. J.; Treves, S. T.; Packard, A. B. Polyhedron 2009, 28, 775-781).

It is also known practice to use cobalt diimine-dioxime complexes as vitamin $B_{12}$ mimics. These complexes are capable of stabilizing either a cobalt-hydride bond, or a cobalt-carbon bond that can undergo homolytic cleavage (cf. Gerli, A.; Sabat, M.; Marzilli, L. G.; *J. Am. Chem. Soc.* 1992, 114, 6711-6718).

The immobilization of one or more complexes on a surface offers many advantages. Specifically, in the case where the immobilized chemical species is a catalyst, its immobilization makes the purification of the final products and the recycling of the catalyst easier by mechanical separation of the immobilized catalyst from the reaction medium. In other cases, immobilization can render a catalyst more stable and thus increase its lifetime and its performance. In a context of electrocatalysis, the immobilization of a catalyst on an electrode can also optimize the flow of electrons from the electrode to the catalyst and thus improve the current densities.

Other applications may moreover require the coupling of a ligand or a complex with another molecule, in order to be able to combine the properties of the two partners. In this respect, mention may be made, for example, of the combination of a polydentate ligand with a fluorescent species. In this case, complexation of the ligand modifies the fluorescence properties of the system, which makes it possible to obtain sensors that give information regarding the presence of metal ions in the medium (cf. Valeur, B.; Leray, I. Coord. Chem. Rev. 2000, 205, 3-40).

The diimine-dioxime ligands that have been the most extensively studied are those with a carbon chain containing two or three atoms between the two nitrogen atoms of the imine functions. This spacing leads, after complexation, to stable 5- or 6-membered metallocycles. As illustrations of ligands of this type, mention may be made of those described in the publication by Dey et al; *Synth, React. Inorg. Met.-Org. Chem.*; 2004, 34; 1615-1634, which bear an occasionally protected hydroxyl function.

Complexes involving these ligands can theoretically lend themselves to covalent coupling with a substrate in several orientations, namely: the axial orientation (i.e. perpendicular to the plane of the ligand) and the equatorial orientation (i.e. in the plane of the ligand). More particularly, the coupling may take place via the diimine-dioxime ligand, and this is then referred to as coupling in the equatorial orientation (i.e. in the plane of the ligand). Alternatively, the coupling may be performed via an axial ligand, and this is then referred to as coupling in the axial orientation (i.e. generally perpendicular to the plane of the ligand).

The inventors have found that, in comparison with immobilization in the axial position via a generally monodentate ligand, the immobilization mode in the equatorial orientation is stabler since the polydentate nature of the diimine-dioxime ligand makes it possible to reduce the probability of detachment of the metal complex.

However, the hydroxyl functions of the abovementioned diimine-dioxime ligands, which are precisely suitable for coupling in the equatorial orientation, in fact prove in practice to be unsuitable for covalent coupling.

Specifically, the formation of an ether via the Williamson reaction, requiring the production of the corresponding alkoxide, is performed under very basic conditions which the diimine-dioxime ligand residue does not withstand. Coupling by esterification is also forbidden due to the saponification equilibrium that draws into doubt the stability of the final structure. Furthermore, the chemistry on this hydroxyl function comes into competition with the hydroxyl functions borne by the oxime functions, which must maintain their integrity so as not to modify the first coordination sphere of the metal complex.

Thus, there is a need for diimine-dioxime ligands or for corresponding metal complexes that can be immobilized stably over time on a surface of a substrate.

There is also a need to prepare molecular assemblies by covalent coupling of diimine-dioxime ligands or of metal complexes thereof with other molecules.

The present invention is directed towards solving all or some of the abovementioned needs.

SUMMARY

According to a first of its aspects, the invention relates to a substrate, at the surface of which is immobilized at least one unit of formula (I):

(I)

in which:
R$_1$ and R$_2$, which may be identical or different, symbolize a group chosen from: —H, a halogen atom, a C$_1$ to C$_{20}$ ether, a linear or branched C$_1$ to C$_{20}$ alkyl chain optionally interrupted with one or more heteroatoms and/or one or more aryl groups, or a C$_5$ to C$_{30}$ aryl group optionally comprising one or more heteroatoms, the said ether, the said alkyl chain and the said aryl group possibly being substituted with at least one of the following groups: —OH, —NH$_2$, —NO$_2$, —COOH, —CONH$_2$, a triazole ring or —COOZ$_1$ with Z$_1$ representing a C$_1$ to C$_5$ alkyl group, a C$_1$ to C$_5$ alkoxy group or a halogen, X is the product of a reaction of "click-chemistry" type, aza-Wittig, peptide coupling or the product resulting from the hydrogenation of the product obtained after the said aza-Wittig reaction, Y is a spacer arm, n is a number equal to 0 or 1, and A:
represents a saturated or unsaturated C$_2$ to C$_3$ hydrocarbon-based chain, or
features a double bond C=C of a C$_5$ to C$_6$ aromatic or heteroaromatic ring to which ring is attached Y, if n=1, or X, if n=0.

The term "reaction of click-chemistry" type" means a coupling reaction between an alkyne function and an azide function.

The term "reaction of peptide coupling type" should be understood as meaning a reaction leading to the formation of an amide by coupling between an amine function and a carboxylic function, or a derivative thereof such as an acyl halide or activated ester function, for instance the hydroxyphthalimide ester.

The expression "substrate at the surface of which is immobilized at least one unit of formula (I)" should be understood as meaning that the unit of formula (I) is present at the surface of the substrate in an accessible form, i.e. suitable for a potential interaction with one or more other molecule(s).

As emerges from the text hereinbelow, this immobilization may be of covalent or non-covalent nature.

According to one embodiment variant of the invention, the unit of structure (I) is advantageously coordinated to at least one metal so as to form at least one metal complex, for example which is capable of showing catalytic activity.

For the purposes of the invention, the term "metal" is intended to denote the following elements: Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg, Ga, In, Sn, Tl, Pb, Bi, Po.

As emerges from the text hereinbelow, the ligands under consideration according to the invention advantageously lend themselves to immobilization on a substrate of the metal complex, formed in part by at least one of the said ligands, via a bond in the equatorial position.

As mentioned hereinabove, in comparison with immobilization in the axial position via a generally monodentate ligand, the mode of immobilization in the accessible equatorial orientation according to the invention advantageously proves to have increased stability especially due to the polydentate nature of the diimine-dioxime ligand, which makes it possible to significantly reduce the probability of detachment of the metal complex.

According to another of its aspects, the invention relates to a ligand of formula (II):

(II)

in which:
R$_1$, R$_2$, A, n and Y are as defined above, and
T symbolizes one of the following groups: N$_3$, NH, or N=P(Ar)$_3$ for which (Ar)$_3$ represents three identical or different, optionally substituted C$_6$ to C$_{20}$ aromatic groups, N=P(Ar)$_3$ preferably being N=PPh$_3$.

According to yet another of its aspects, the invention relates to a ligand of formula (III):

(III)

in which:
R$_1$, R$_2$, A, n, X and Y are as defined above,
m is a number equal to 0 or 1,
P symbolizes a C$_1$ to C$_{20}$ hydrocarbon-based chain comprising, where appropriate, one or more heteroatoms, optionally interrupted with one or more aryl groups, a C$_1$ to C$_{20}$ ether, a C$_1$ to C$_{20}$ ester or a C$_5$ to C$_{30}$ aryl group optionally comprising one or more endocyclic heteroatoms, P may, where appropriate, be substituted with at least one of the following groups: —OH, —NH$_2$, —NO$_2$, —COOH, —CONH$_2$ or —COOZ$_2$ with Z$_2$ representing a C$_1$ to C$_5$ alkyl group, a C$_1$ to C$_5$ alkoxy group or a halogen, and F symbolizes a reactive function that is capable of forming a covalent or non-covalent bond and in particular chosen from: —COOH, —NH$_2$, —N$_3$, —C≡CH, and a silane group chosen from: a trihalosilane group, a trihydrogenosilane group, a trialkoxysilane group —Si(OR$_5$)$_3$- with R$_5$ representing a linear or branched alkyl group of 1 to 6 carbon atoms, a phenyl group, a triaminoalkoxysilane group —Si(NR$_6$R$_7$)$_3$, with R$_6$ and R$_7$ representing, independently of each other, a linear or branched saturated alkyl group of 1 to 6 carbon atoms, a phenyl group or an organometallic group.

According to another of its aspects, the invention relates to an electrode comprising a substrate as defined above.

According to another of its aspects, the invention relates to an electrolysis device comprising an electrode as defined above.

According to another of its aspects, the invention relates to a process for producing dihydrogen using an electrolysis device as defined above.

According to another of its aspects, the invention relates to a process comprising at least the steps consisting in:
providing a functionalized substrate as defined above and also a source of metal ions to be analyzed, and
placing the said substrate in contact with the said source of metal ions under conditions suitable for coordination of the metal ions by the unit (I).

This process may be a process for detecting metal ions, the coordination of the metal ions by the unit (I) then possibly leading to the modification of at least one property of the substrate. This coordination may, for example, lead to the modification of an optical property of the substrate, especially the modification of its fluorescence spectrum, or the modification of an electrochemical property of the substrate, especially the modification of its voltammogram due to the presence of the complexed metal ions.

In this case, the process may also comprise a consecutive step for characterizing the optical or electrochemical behavior of the said substrate, especially by reference to a control value.

The process described above may also be a process for extracting metal ions and, after the complexation, the contact may be interrupted between the substrate and the solution of metal ions so as to extract the complexed metal ions.

Unit of Formula (I)

It is understood that the implementation examples given below for R$_1$, R$_2$, A and Y apply to the units of formula (I) and also to the ligands of formulae (II) and (III).

Moreover, the implementation examples given below for X apply to the units of formula (I) and to the ligands of formula (III).

Preferably, the unit of formula (I) may have one of the following formulae:

(IA)

(IB)

(IC)

in which R$_1$, R$_2$ and X may be as defined above.

In one particularly preferred variant, the unit of formula (I) may be of formula:

(IA)

in which R$_1$, and X may be as defined above.

Definition of X

X may, preferably, be of formula:

(IIA)

(IIB)

(IIC)

(IID)

(IIE)

in which:
* symbolizes a bond to Y if n=1 or to A if n=0, and
$R_3$ and $R_4$ are chosen from: —H, a $C_1$ to $C_{20}$ alkyl chain, a $C_1$ to $C_{20}$ ether, a $C_1$ to $C_{20}$ ester or a $C_1$ to $C_{30}$ aryl group, $R_3$ and $R_4$ being, where appropriate, substituted with at least one of the following groups: —OH, —$NH_2$, —COOH or —$CONH_2$.

When X is of formula (IIE), the unit (I) is advantageously coordinated to at least one metal.

In an even more preferred variant, X may be of formula:

(IIA)

(IIB)

in which * is as defined above.

Definition of Y

Y is a spacer arm whose function is to bond X to A when n is equal to 1.

When n is equal to 1, Y may be chosen, for example, from a linear or branched $C_1$ to $C_{20}$ alkyl chain optionally interrupted with one or more heteroatoms and/or one or more aryl groups, a $C_1$ to $C_{20}$ ether, a $C_1$ to $C_{20}$ ester or a $C_5$ to $C_{30}$ aryl group optionally comprising one or more heteroatoms, Y may, where appropriate, be substituted with at least one of the following groups: —OH, —$NH_2$, —$NO_2$, —COOH, —$CONH_2$ or —$COOZ_2$ with $Z_2$ representing a $C_1$ to $C_5$ alkyl group, a halogen or a $C_1$ to $C_5$ alkoxy group.

Definition of A

For its part, A may preferably be a saturated $C_2$ to $C_3$ hydrocarbon-based chain.

In an even more preferred variant, A may be a saturated $C_3$ hydrocarbon-based chain.

Definition of $R_1$ and $R_2$

The two units $R_1$ may be identical or different. Similarly, the two units $R_2$ may be identical or different.

$R_1$ and $R_2$ may be, for example, identical or different and chosen from: —H or a $C_1$ to $C_{20}$ alkyl chain optionally substituted with at least one of the following groups: —OH, —$NH_2$, —COOH, —$CONH_2$ or a triazole ring.

$R_1$ and $R_2$ may, for example, be identical.

$R_1$ and $R_2$ may, for example, both be chosen from optionally substituted $C_1$ to $C_{20}$ alkyl chains.

$R_1$ and $R_2$ may, for example, both be optionally substituted methyl groups.

The unit of formula (I), which may or may not be coordinated to a metal, may be directly bonded to the substrate.

In this case, the immobilization process depends on the nature of the reactive extremity(ies) of the substrate, on the one hand, and that of the diimine-dioxime derivative, on the other hand.

With regard to the nature of the substrate, the unit (I), which may or may not be coordinated to a metal, may be covalently or non-covalently bonded to the substrate.

As a variant, the unit of formula (I) may be bonded to the substrate via a linker arm, also referred to as L.

Definition of the Linker Arm

In this case, the immobilization process depends on the nature of the reactive extremity(ies) of the substrate, on the one hand, and on that (those) of the linker arm, on the other hand.

The linker arm may be immobilized on the substrate so as to ensure good electron transfer between the substrate and the unit (I) optionally coordinated by a metal.

The linker arm may be covalently or non-covalently bonded to the substrate.

The non-covalent interaction may preferably be an electrostatic interaction or a π-π interaction.

In addition, the linker arm may be bonded to one or more units of formula (I).

The unit of formula (I), which may or may not be coordinated to a metal, may, for example, be covalently bonded to the linker arm.

For obvious reasons, the choice of linker arm and more particularly of the units present at its extremities is linked to the nature of the substrate and also to the reactive function present on the diimine-dioxime derivative to be immobilized.

It is within the scope of a person skilled in the art to adjust the chemical nature of the two reactive extremities of the linker arm so as to allow the creation of bonds on the substrate and on the unit (I), respectively.

When the unit of formula (I) is bonded to the substrate via a linker arm, a unit of formula (I') below may be immobilized on the surface of the substrate, (I')

in which:
R$_1$, R$_2$, A, Y, n and X are as defined above,
L symbolizes the linker arm, and
*** symbolizes a bond to the substrate.

The chemical nature of the linker arm L is not a deciding factor as long as it does not excessively disrupt the properties, especially in terms of reactivity or catalysis, of the unit (I) and of its complexes.

By way of illustration, the linker arm may be, for example, of formula (IV) or (V):

in which:
* is as defined above and ** symbolizes a bond to X,
Ar symbolizes a C$_6$ to C$_{30}$ aryl group optionally substituted with at least one of the following groups: —OH, —NH$_2$, —COOH, —CONH$_2$ or a triazole ring, Ar being capable of establishing an interaction featured by - - - -, which is covalent or non-covalent, with the substrate, and
B is a divalent hydrocarbon-based group optionally interrupted with a unit: —COO— or —CONH— and whose extremity attached to X is formed from a unit resulting from coupling between two reactive functions, for instance an amide, ester or ether unit.

B may, for example, comprise an extremity bonded to X featured by an ether unit.

When the linker arm is of formula (IV), it may, for example, be covalently bonded to the substrate.

When the linker arm is of formula (IV), the bond between the said arm and the substrate may, for example, be obtained via a reduction reaction of aryldiazonium salts.

When the linker arm is of formula (V), it may be non-covalently bonded to the substrate, for example by an electrostatic interaction.

It is manifest that the preparation of a substrate in accordance with the present invention falls within the competence of a person skilled in the art.

According to one implementation example, such a substrate may be obtained via a process comprising at least the steps consisting in:
a) bonding the linker arm to the substrate, and
b) bonding the linker arm to the unit (I), the unit (I) possibly being coordinated to a metal,
step a) taking place before or after step b).

Metal Complexes

As mentioned above, the unit of structure (I) may be coordinated to at least one metal so as to form at least one metal complex.

As stated above, the metal is chosen from: Sc, Ti, V, Cr, Mn, Fe, Co, Ni, Cu, Zn, Y, Zr, Nb, Mo, Tc, Ru, Rh, Pd, Ag, Cd, Hf, Ta, W, Be, Os, Ir, Pt, Au, Hg, Ga, In, Sn, Tl, Pb, Bi or Po.

The metal may preferably be a transition metal from the Periodic Table.

In one particularly preferred variant, the metal is chosen from nickel (Ni) and cobalt (Co).

In one particularly preferred variant, the metal complex formed with the said unit of formula (I) may have one of the following formulae:

in which Z denotes a halogen atom, preferably chlorine or bromine, and ** symbolizes the bond to X via Y if n=1.

Substrate

For the purposes of the invention, the substrate may comprise, for example may consist of, a material or may consist of one or more molecules of interest.

In the variant in which the substrate comprises, or even consists of, a material, this material may comprise a conductive or semiconductive material with a high specific surface area.

This conductive or semiconductive material with a high specific surface area may be deposited on a conductive support so as to form an electrode with a high specific surface area.

The conductive support may comprise, for example may be formed from, ITO (Indium Tin Oxide), or another conductive transparent oxide such as F:SnO$_2$ (Fluorine Tin Oxide) or Al:ZnO (aluminum-doped ZnO), stainless steel, iron, copper, nickel, cobalt, aluminum, gold, doped diamond, titanium, brass or carbon, for example graphite. The conductive support may preferably comprise, for example may consist of, ITO or graphite.

When the substrate comprises, or even consists of, a material, this material may be chosen from:
semiconductive oxides, for example: ITO (Indium Tin Oxide), FSnO$_2$ (Fluorine Tin Oxide), ZnO, Al:ZnO (aluminum-doped ZnO), Na:ZnO (sodium-doped ZnO), NiO or TiO$_2$, or
conductive or semiconductive materials, for example:
metals, for example silicon, optionally doped, brass, stainless steel, iron, copper, nickel, cobalt, aluminum, silver, gold, titanium,
metal oxides, or
carbon-bused materials, for example single-wall or multi-wall carbon nanotubes, carbon black, fullerene nanoparticles, graphite, vitreous carbon, graphene or doped diamond.

The material at least partly constituting the substrate may be solid or semisolid.

The material at least partly constituting the substrate may or may not be nanostructured.

The term "nanostructured material" should be understood as meaning either that the material has substantial surface roughness and/or a high specific surface area, or that it may be totally or partly formed from particles, for example with a diameter of between 2 nm and 10 μm and in particular between 5 nm and 300 nm.

As mentioned above, the substrate may, as a variant, be formed from one or more molecules of interest, especially one or more biological molecules, chosen, for example, from: markers, dyes, fluorophores (for instance coumarins, fluorescein, modified fluoresceins, rhodanins, iguanins, borondipynomethene, oxazines and the like), radiolabeled molecules, contrast agents (X-rays, MRI), toxins (including cytotoxins), linkers, therapeutic, cosmetic or plant-protection active agents, members of a specific bonding pair, peptides, amino acids and amino acid residues, polypeptides (including peptides and proteins), sugars and sugar residues, oligonucleotides, DNA or RNA strands, antibodies, antigens, compounds with cis-trans isomerism such as diarylethylene derivatives, spiropyrans, spiroxazines, fulgides or azobenzene (whose presence on a surface is particularly useful for the manufacture of light-controlled molecular switches).

The molecule of interest may preferably be a fluorophore.

According to one preferred variant, the molecule of interest is a biological molecule.

The biomolecules of interest may be of natural origin or produced synthetically or in a recombinant manner and may be isolated and purified.

When the molecule of interest is a polypeptide, the polypeptide may be composed of D or L amino acids, or both, and may also be modified, whether naturally, synthetically or in a recombinant manner, no as to include other groups therein. For example, the target polypeptide may be a lipoprotein, a glycoprotein or any other modified protein.

According to another embodiment variant, the molecule of interest may be a contrast agent.

EXAMPLES

The NMR spectra described in the examples were recorded at room temperature in tubes 5 mm in diameter on a Bruker AC 300 spectrophotometer. The residual peaks of the not completely deuterated solvent were used as internal references.

The mass spectra (electrospray ionization) described in the examples were measured on a Finnigan LCQ thermoquest machine of "ion-trap" type.

The electrochemical measurements described in the examples were taken in a conventional manner with a three-electrode assembly and an EG&G potentiostat, model 273A. The auxiliary electrode is a platinum wire, the reference electrode is an Ag/AgCl, 3M KCl electrode. The working electrode is either a vitreous carbon electrode or a functionalized ITO blade, or an electrode based on carbon nanotubes described in: Le Goff et al., M. Science 2009, 326, 1384-1387. The potentials are occasionally given relative to the ferricinium/ferrocene couple ($Fc^+/Fc$) which was remeasured by adding ferrocene to the electrolyte at the end of the manipulation. The electrolyte is a 0.1 M solution of tetrabutylammonium tetrafluoroborate in acetonitrile.

Example 1

Figure 1:
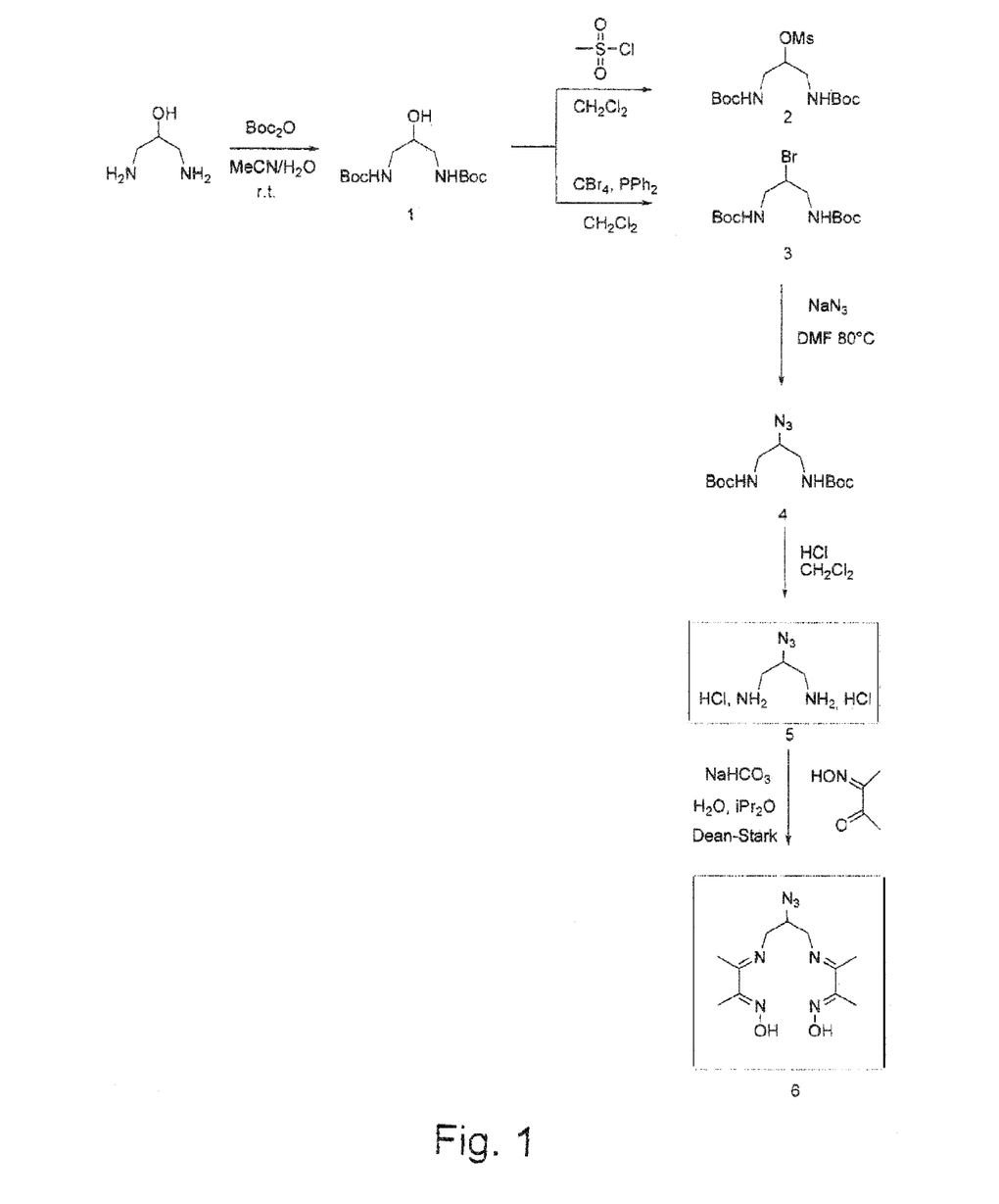
FIG. 1 illustrates a scheme for the synthesis of a diimine-dioxime ligand according to the invention.

Synthesis of a Ligand of Formula (II) Having an Attachment Function T of Azide Type FIG. 1 summarizes the synthetic route used for obtaining the diimine-dioxime ligand 6 containing an azide group T, a group A of saturated $C_3$ hydrocarbon-based chain type and substituents $R_1$=Me and $R_2$=Me.

Synthesis of N,N'-Di-t-boc-2-hydroxy-1,3-diaminopropane (1)

To a solution of 2-hydroxy-1,3-diaminopropane (5 g, 55 mmol) in 100 ml of an $MeCN/H_2O$ mixture (5/5) is added a solution of di-t-butyl carbonate (26 ml, 113 mmol) in MeCN at 0° C. The temperature of the mixture is then allowed to rise to room temperature and the mixture is kept stirring for 18 hours. The solution is then extracted with $CH_2Cl_2$ (200 ml) and the organic phase is washed with saturated aqueous $NaHCO_3$ solution (3×50 ml), dried over $MgSO_4$ and then concentrated under reduced pressure. A white solid (14.7 g, 51 mmol) is collected.

$^1$H NMR (300 MHz, $CDCl_3$): δ (ppm) 5.34 (s, 2H, NH); 4.00 (bs, 1H, OH), 3.72 (m, 1H, C(OH)H); 3.16 (m, 4H, $CH_2$), 1.40 (s, 18H, $^t$Boc).

Synthesis of N,N'-Di-t-boc-2-methanesulfonyl-1,3-diaminopropane (2)

To a solution of 1 (4 g, 14 mmol) in $CH_2Cl_2$ (100 ml) under Ar containing $Et_3N$ (2.9 ml, 20 mmol) cooled to 0° C. is added dropwise methanesulfonyl chloride (2.15 ml, 28 mmol). The temperature of the mixture is then allowed to rise to room temperature, and the mixture is kept stirring for 2 hours. Next, a further 2 equivalents of methanesulfonyl chloride (2.15 ml, 28 mmol) are added to the mixture precooled to 0° C. The mixture is stirred at room temperature for 18 hours and then extracted with saturated aqueous $NaHCO_3$ solution (5×50 ml), and the organic phase is dried over $MgSO_4$ and concentrated under reduced pressure. A white solid (4.8 g, 13 mmol) is collected.

$^1$H NMR (300 MHz, $CDCl_3$): δ (ppm) 5.18 (bs, 2H, NH); 4.68 (m, 1H, C(OMs)H); 3.49 (m, 2H, $CH_2$); 3.33 (m, 2H, $CH_2$); 3.11 (s, 3H, OMs); 1.46 (s, 18H, $^t$Boc).

Synthesis of N,N'-Di-t-boc-2-bromo-1,3-diaminopropane (3)

To a solution of 1 (2.9 g, 9.3 mmol) in $CH_2Cl_2$ (30 ml) containing $PPh_3$ (2.93 g, 1.1 mmol) cooled to 0° C. is added $CBr_4$ (3.7 g, 11.1 mmol) dissolved in $CH_2Cl_2$ (20 ml). The solution is stirred for 2 hours at 0° C. and then for 3 hours at room temperature. The solvent is evaporated off under reduced pressure and the product is purified by chromatography on silica gel. A first wash with pentane removes impurities, and the product is then eluted with a 7/3 pentane/EtOAc mixture. A white solid is collected (2.2 g, 6.3 mmol).

$^1$H NMR (300 MHz, $CDCl_3$): δ (ppm) 5.32 (bs, 2H, NH); 4.11 (m, 1H, CHBr), 3.74 (m, 2H, $CH_2$); 3.27 (m, 2H, $CH_2$); 1.47 (s, 18H, $^t$Boc).

Synthesis of N,N'-Di-t-boc-2-azide-1,3-diaminopropane (4)

To a solution of 2 (5 g, 14 mmol) in dry DMF (20 ml) is added NaN$_3$ (3.54 g, 54 mmol) suspended in dry DMF (10 ml). The mixture is heated at 80° C. for 18 hours. Next, water (100 ml) and CH$_2$Cl$_2$ (100 ml) are added to the mixture, and the organic phase is then washed with water (3×50 ml). The organic phase is dried over MgSO$_4$ and concentrated under vacuum. A yellow oil (3.2 g, 10 mmol) is collected.

$^1$H NMR (300 MHz, CDCl$_3$): δ (ppm) 5.07 (bs, 2H, NH); 3.66 (m, 1H, CHN$_3$); 3.38 (m, 2H, CH$_2$); 3.16 (m, 2H, CH$_2$); 1.47 (s, 18H, $^t$Boc).

The same protocol may be applied using 3 instead of 2 as starting material.

Synthesis of 2-azide-1,3-diaminopropane hydrochloride salt (5)

HCl gas is bubbled into a solution of 4 (2 g, 6.3 mmol) in CH$_2$Cl$_2$ at 0° C. for 2 hours. The white precipitate is then filtered off and washed with Et$_2$O, and then dried under vacuum (1.13 g, 6.0 mmol).

$^1$H NMR (300 MHz, D$_2$O): δ (ppm) 4.16 (m, 1H, CHN$_3$), 3.27 (m, 2H, CH$_2$); 3.04 (m, 2H, CH$_2$).

Synthesis of N$^2$,N$^{2'}$-2-azidepropanediylbis(2,3-butadione-2-imine-3-oxime) (6)

A solution of 5 (200 mg, 1.1 mmol), 2,3-butadione monoxime (216 mg, 2.2 mmol) and NaHCO$_3$ (180 mg, 2.2 mmol) in a two-phase mixture of water (5 ml) and $^i$Pr$_2$O (20 ml) is refluxed for 18 hours using Dean-Stark apparatus. Next, the mixture is hot-filtered and the precipitate is washed with CH$_2$Cl$_2$. The solvent is evaporated off, and the solid is dissolved in a minimum amount of EtOAc and precipitated by adding pentane, filtered off and dried under vacuum.

$^1$H NMR (300 MHz, DMSO): δ (ppm) 11.54 (s, 2H, NOH); 4.02 (m, 1H, CHN$_3$); 3.62 (m, 4H, CH$_2$); 2.02 (s, 3H, CH$_3$); 1.94 (s, 3H, CH$_3$).

If the reaction is incomplete, the whole material is taken up in distilled EtOH, and ethyl orthoformate is added to the mixture, which is then refluxed for 8 hours. The solvent is then evaporated off and the product is precipitated from pentane.

Example 2

This example concerns the preparation of complexes whose formulae are given below:

X: Cl (7), Br (8)

9

Transition metals such as cobalt or nickel may be complexed with the functionalized tetradentate ligand obtained in Example 1.

Synthesis of the Complex [Co(DO)(DOH)N$_3$pnCl$_2$] (7)

To a solution of 6 (50 mg, 0.18 mmol) in acetone (20 ml) is added a solution of CoCl$_2$.6H$_2$O (42.5 mg, 0.18 mmol) in acetone (5 ml). On sparging with air, the brown mixture becomes green. After 30 minutes, the solvent is evaporated off and a green solid is collected. It is taken up first in acetone and then in dichloromethane to give 7 (92 mg, 0.18 mmol).

$^1$H NMR (300 MHz, acetone d$^6$): δ (ppm) 19.39 (s, 1H, OHO); 4.56 (m, 3H, CH$_2$, CHN$_3$); 3.90 (t, 13.2 Hz, 2H, CH$_2$); 2.77 (s, 6H, CH$_3$); 2.55 (s, 6H, CH$_3$).

Synthesis of the Complex [Co(DO)(DOH)N$_3$pnBr$_2$] (8)

The same procedure as for 7 is applied using CoBr$_2$.6H$_2$O.

$^1$H NMR (300 MHz, acetone d$^6$): δ (ppm) 19.45 (s, 1H, OHO); 4.70 (m, 3H, CH$_2$, CHN$_3$); 3.89 (m, 2H, CH$_2$); 2.80 (s, 6H, CH$_3$); 2.57 (s, 6H, CH$_3$).

Synthesis of the Complex [Ni(DO)(DOH)N$_3$pn]ClO$_4$ (9)

To a solution of 6 (50 mg, 0.18 mmol) in MeOH (20 ml) is added an excess of NiCl$_2$ (60 mg, 0.25 mmol) dissolved in MeOH (5 ml). After 30 minutes, the mixture is filtered and the filtrate is concentrated under reduced pressure and the residue taken up in water. The Ni complex is precipitated by adding NaClO$_4$ solution. The orange solid is recovered by filtration (35 mg, 0.08 mmol).

$^1$H NMR (300 MHz, acetone d$^6$): δ (ppm) 18.28 (s, 1H, OHO); 4.63 (m, 1H, CHN$_3$); 3.90 (m, 2H, CH$_2$); 3.70 (d, J: 15.9 Hz, 2H, CH$_2$); 2.47 (s, 6H, CH$_3$); 2.21 (s, 6H, CH$_3$).

$^{13}$CH NMR (75 MHz, acetone d$^6$): 179.3 (CNOH); 156.2 (CN); 58.6 (CH); 50.6 (CH$_2$); 16.5 (CH$_3$); 11.5 (CH$_3$).

Table 1 below shows the crystallographic parameters of complexes (7) and (9) obtained.

TABLE 1

| Compound | [Co(DO)(DOH)N$_3$pnCl$_2$] | [Ni(DO)(DOH)N$_3$pn](ClO$_4$) |
|---|---|---|
| Formula | C$_{11}$H$_{18}$Cl$_2$CoN$_7$O$_2$ | C$_{11}$H$_{18}$ClN$_7$NiO$_6$ |
| Molecular mass | 425.15 | 338.48 |
| Color | Green | Brown |
| Crystal size | 0.93 × 0.73 × 0.33 mm | 0.66 × 0.41 × 0.29 mm |
| Crystalline system | Monoclinic | Orthorhombic |
| Space group | P1 2$_1$/n 1 | P 2$_1$ 2$_1$ 2$_1$ |
| a [Å] | 10.0677 (19) | 6.8991 (2) |
| b [Å] | 14.6157(3) | 11.7274 (3) |

TABLE 1-continued

| | | |
|---|---|---|
| c [Å] | 11.4658 (2) | 20.7645 (6) |
| α [°] | 90 | 90 |
| β [°] | 97.5274 (18) | 90 |
| γ [°] | 90 | 90 |
| V [Å]$^3$ | 1672.62 (5) | 1680.02 (9) |
| Z | 4 | 4 |
| $\rho_{calcd}$ [mg m$^{-3}$] | 1.688 | 1.734 |
| μ [mm$^{-1}$] | 1.372 | 1.361 |
| Collected reflections | 9728 | 23236 |
| Single reflections ($R_{int}$) | 5026 ($R_{int}$ = 0.0187) | 12364 ($R_{int}$ = 0.0291) |
| Observed reflections [I > 2σ(I)] | 3785 | 6843 |
| Number of refined parameters | 273 | 278 |
| Indices R (all reflections) | R1 = 0.0455, wR2 = 0.0771 | R1 = 0.0987, wR2 = 0.1394 |
| Indices R (observed reflections) | R1 = 0.0307, wR2 = 0.0744 | R1 = 0.0547, wR2 = 0.1296 |
| Refinement quality S | 1.015 | 0.961 |
| Δρ (max/min) [e Å$^{-3}$] | 0.595 and −0.370 | 0.957 and −1.047 |

Figure 2:
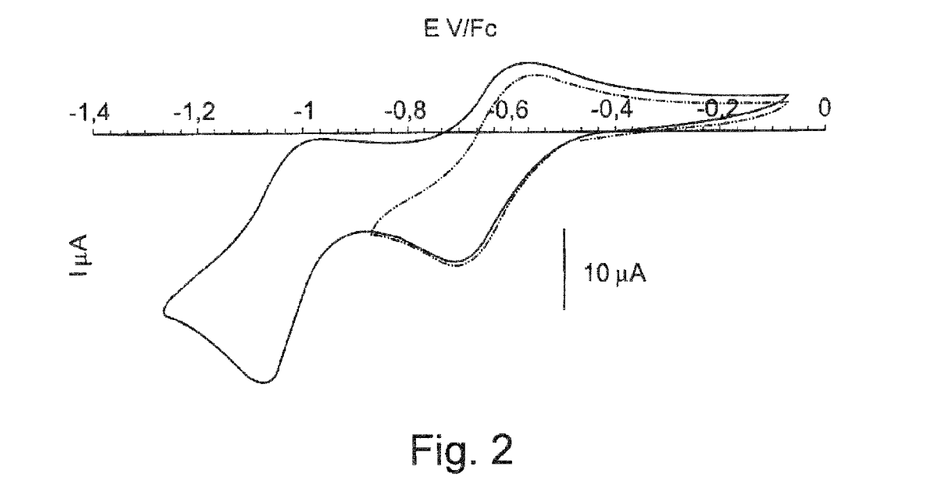
FIGS. 2 and 3 represent cyclic voltammetry analyses of metal complexes.
Figure 3:
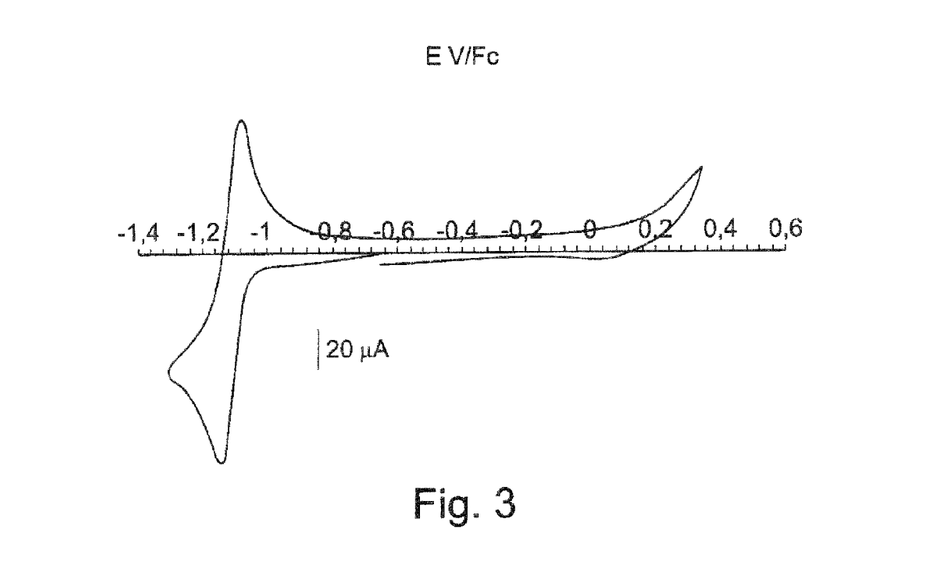

FIGS. 2 and 3 show the cyclic voltammograms of compounds 7 and 9 recorded at 100 mV.s$^{-1}$ in acetonitrile on a vitreous carbon electrode (solution of complex at 1 mM in acetonitrile and at 0.1 M of tetrabutylammonium tetrafluoroborate).

The electrochemical potentials are given relative to the ferrocene-ferricinium couple.

Example 3

Synthesis of a Metal Complex Using a Ligand of Formula (II) with a Group T of the Type —N=PPh$_3$ The reaction of complex 9 with triphenylphosphine in THF leads to the formation of the phosphine-imine compound 10a, which was characterized by $^1$H NMR and by mass spectrometry.

The protocol for synthesizing the complex Ni(DO)(DOH)(CH$_2$CH(—N=PPh$_3$)CH$_2$)]ClO$_4$ 10a is as follows: in a round-bottomed flask, 35 mg of the nickel complex 9 and 21 mg of triphenylphosphine are dissolved in 10 ml of THF (undistilled). After stirring for 24 hours, the THF is evaporated off and the residue is washed with water and then air-dried.

$^1$H NMR (300 MHz, acetone d$^6$): δ (ppm) 2.1 (s, 6H); 2.8 (s, 6H); 3.55-3.65 (m, 4H); 4.21 (m, 1H); 7.71-7.94 (m, 15H); 18.33 (s, 1H). ESI-MS: m/z: 572.3.

Example 4

Synthesis of a Metal Complex Using a Ligand of Formula (II) Containing a Group T of —NH$_2$ Type

The hydrolysis of 10a by prolonged standing in a THF/water mixture leads to the corresponding amino derivative 10b.

The protocol for synthesizing the complex Ni(DO)(DOH)(CH$_2$CH(—NH$_2$)CH$_2$)]ClO$_4$ 10b is as follows: in a round-bottomed flask, 40 mg of the nickel complex 10a are dissolved in 10 ml of THE (undistilled) and 4 ml of deionized water. After stirring for 24 hours, the THF is evaporated off and the residue is washed with water and then air-dried.

Example 5

Synthesis of Metal Complexes Using Ligands of Formula (III)

The synthetic schemes corresponding to this example are given below.

-continued

The cyclooctyne 14 was synthesized according to a procedure described in the publication: Agard, N. J.; Baskin, J. M.; Prescher, J. A.; Lo, A.; Bertozzi, C. R.; A comparative study of bioorthogonal reactions with azides. *Acs Chemical Biology* 2006, 1, (10), 644-648 and patent application US 2006/0110782.

In this approach, two isomers are formed during the reaction. The above schemes show the reaction products of complexes 7, 8 and 9 with the cyclooctyne 14.

The protocol corresponding to the top scheme is as follows: to a solution of 12 mg ($6.6 \times 10^{-5}$ mol; 1 eq.) of cyclooct-1-yn-3-glycolic acid 14 in THF is added a solution of 27 mg ($6.6 \times 10^{-5}$ mol; 1 eq.) of cobalt complex 7 in ethanol. The reaction mixture is stirred for 18 hours at room temperature. The organic solvents are then evaporated off under reduced pressure. The product is purified on a Sephadex size exclusion column.

The protocol corresponding to the bottom scheme is as follows: to a solution of 12 mg ($6.6 \times 10^{-5}$ mol; 1 eq.) of cyclooct-1-yn-3-glycolic acid 14 in THF is added a solution of 29 mg ($6.6 \times 10^{-5}$ mol; 1 eq.) of the nickel complex 9 dissolved in acetone. The reaction mixture is stirred for 18 hours at room temperature. The reaction medium is concentrated under reduced pressure and then air-dried. The product is purified on a Sephadex size exclusion column.

Example 6

Immobilization by Huisgen Cycloaddition on an ITO Surface of a Coordination Complex The Huisgen coupling may be performed on an ITO surface prefunctionalized with a cyclooctyne function.

The ITO blades used are obtained from Präzisions Glas & Optik GmbH, Germany, reference CEC005S, resistivity ≤5 ohms/sq as defined in a known manner for conductive thin layers. The ITO is deposited on a glass substrate 1.1 mm thick and passivated with a thin layer of $SiO_2$.

Preparation of the Surface of the ITO Blades

The blades are washed by ultrasonication for 5 minutes in acetone and are then activated by ultrasonication for 30 minutes in an NaOH solution (0.1 M) in an ethanol/water mixture (43/57).

The blades are then rinsed with deionized water and dried under a stream of argon.

Immediately after, the blades undergo an oxygen plasma treatment. The machine is set to deliver a power of 60 watts at 0.5 Torr for 6 minutes.

Functionalization of the ITO Blades with Cyclooctyne 14

The ITO blades that have undergone the surface treatment described above are immersed in a solution of 20 mg of cyclooctyne 14 in 15 ml of toluene and placed at 100° C. for 20 hours in the oven in a closed system. They are then rinsed with deionized water and with acetone, and dried under argon.

Immobilization of the molecule 14 on the ITO surface is then obtained via the formation of electrostatic interactions between the oxygen atoms of the carboxylate unit of 14 and the hydroxyl functions and/or the surface metal cations.

Coupling of the Complex 7

The ITO blades thus functionalized are then immersed in a solution of 6 mg of complex 7 dissolved in a mixture of 4 ml of distilled water/methanol (1/1) (cf. scheme). The solution is stirred for 12 hours. The blades are then rinsed with distilled water and with acetone.

The XPS (photoelectron spectroscopy) analyses of the surface obtained confirm the presence of cobalt, which is absent when the surfaces are analyzed before reaction with 7. This functionalization withstands washing with distilled water and ultrasonication.

Example 7

Immobilization of a Coordination Complex on a Lawn of Carbon Nanotubes

The scheme below illustrates the reactions performed in the context of this example.

The functionalization procedure proceeds firstly by immobilization of carbon nanotubes on a carbon fiber electrode covered with a microporous conductive coating (gas diffusion layer). The carbon nanotubes are then decorated with amine functions.

The cobalt complex 7 is finally immobilized on the decorated carbon nanotube lawn and deposited on the gas diffusion layer.

1) Functionalization of the Carbon Nanotubes

The gas diffusion layers (BASF LT1200W) are supplied by BASF.

The C100 multiwall carbon nanotubes (>95%) were purchased from Arkema and used without an additional purification step.

The electrodes covered with carbon nanotubes (NTCs/GDL 15 cm$^2$; 0.1 mg$_{NTCs}$.cm$^{-2}$) were prepared from gas diffusion layers (BASF) and functionalized by electroreduction of the diazonium salt (4-(2-aminoethyl)benzenediazonium tetrafluoroborate).

The electrodes covered with carbon nanotubes were used as working electrodes in a three-electrode cell in the presence of 4-(2-aminoethyl)benzenediazonium tetrafluoroborate (1 mmol/L). Three cycles of cyclic voltammetry, performed at 20 mV/s and between 0.4 V and −0.4V vs Fc/Fc$^+$, make it possible to observe at a potential of −0.26 V vs Fc/Fc$^+$, 0.01 mol/L, the reduction of the diazonium salt, resulting in the decoration of the electrodes with amine functions.

The electrodes are then rinsed with acetonitrile by dipping for 30 minutes and then air-dried for several hours before use.

2) Immobilization on the Nanotubes of the Coordination Complex

In a second stage, the amine functions obtained previously are reacted with a cyclooctyne 15 functionalized with an activated ester function in the presence of triethylamine (cf. scheme). The complex 7 is then immobilized via a Huisgen coupling and proves to be active for the reduction of the proton to dihydrogen.

1,3-Dioxoisoindolin-2-yl 2-(cyclooct-2-ynyloxy)acetate 15 is synthesized according to the following protocol: to a solution of 84 mg (1 eq.) of cyclooct-1-yn-3-glycolic acid 14 in 15 ml of ethyl acetate are added 80 mg (1 eq.) of N-hydroxyphthalimide and 101 mg (1 eq.) of N,N'-dicyclohexylcarbodiimide. After stirring for 12 hours at room temperature, the mixture is filtered and the filtrate is purified, after concentration, by column chromatography (90/10 cyclohexane/ethyl acetate). 143 mg of product are recovered in the form of a white solid.

$^1$H NMR (300 MHz, CDCl$_3$): 1.3-2.3 (m, 10H); 4.48 (m, 1H); 4.57 (d, j=17 Hz, 2H); 7.85 (m, 4H)

$^{13}$C NMR (75 MHz, CDCl$_3$): 20.71; 26.09; 29.58; 34.23; 42.17; 55.74; 63.98; 90.78; 102.39; 124.04; 128.83; 134.87; 161.58; 166.77

The gas diffusion layers covered with carbon nanotubes functionalized with amine functions are then immersed for 2 days in a solution of 15 (10 mg) and Et$_3$N (10 µl, 3 mM) in CH$_2$Cl$_2$ (25 ml). The electrodes are then washed by dipping in a solution of CH$_2$Cl$_2$ and air-dried.

The electrodes are then immersed for one week in a solution of 7 (5 mg) in ethanol (25 ml) and then washed by dipping three times successively (30 min, 25 ml) in ethanol. The electrodes thus obtained are finally air-dried.

Figure 4A:
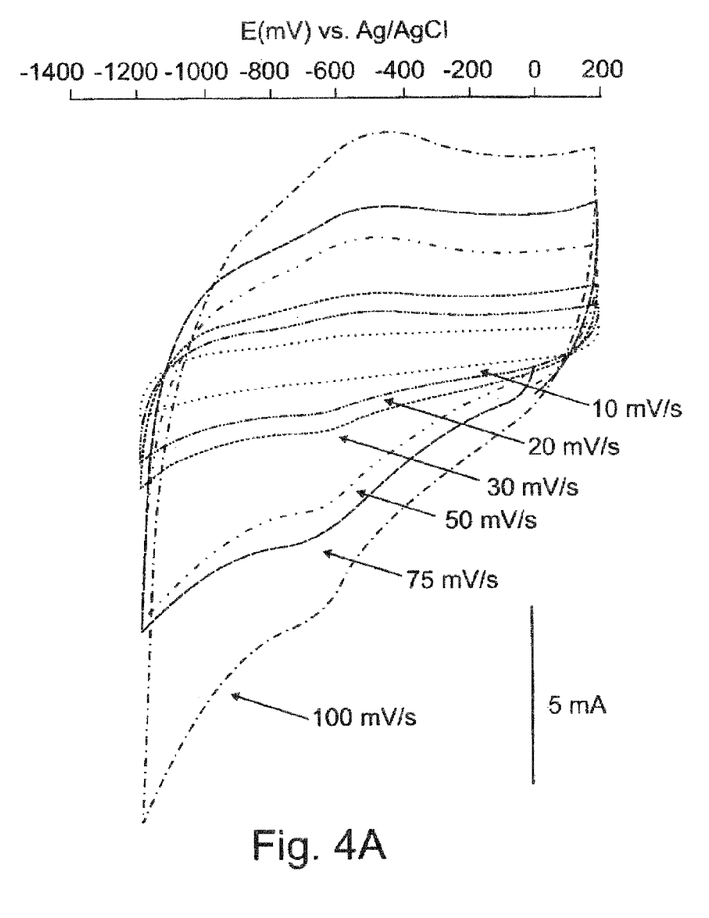
FIGS. 4A and 5 represent cyclic voltammograms recorded on a substrate according to the invention.
Figure 4B:
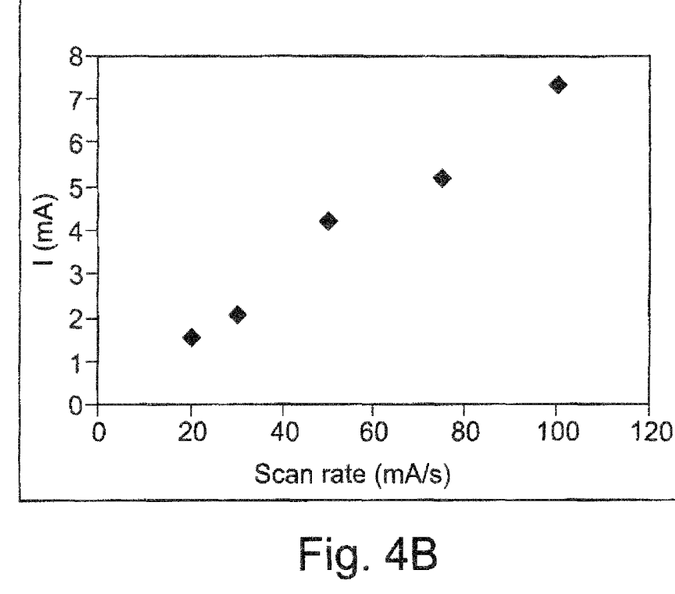
FIG. 4B is a graph drawn from the results illustrated in FIG. 4A.

The cyclic voltammograms, recorded in acetonitrile, on an electrode of carbon nanotubes functionalized with the cobalt diimine-dioxime complex are given in FIG. 4A. The presence of a reversible electrochemical wave at −600 mV vs Ag/AgCl is the signature of the cobalt diimine-dioxime complex. The change in peak currents is proportional to the sweep speed (cf. FIG. 4B), which is indicative of an electroactive unit immobilized (and not adsorbed) onto the surface of the working electrode.

Figure 5:
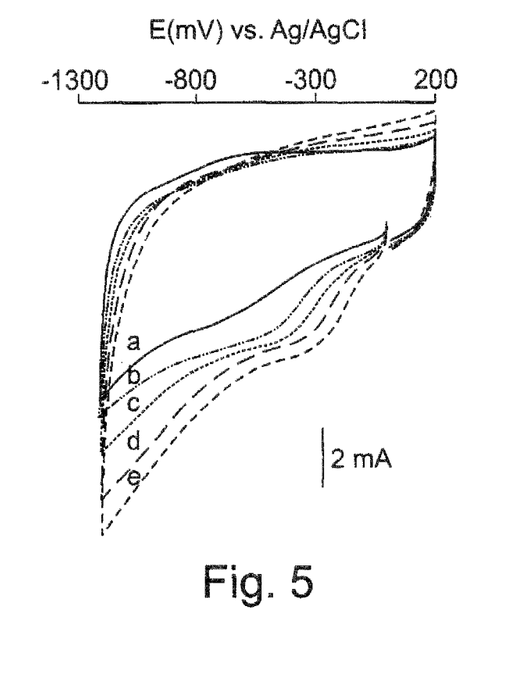

The voltammogram of FIG. 5 shows the change of this voltammogram when anilinium tetrafluoroborate is added as a solution. This acid is used as a proton source. It is noted that the electrochemical wave shifts towards the positive potentials and increases in intensity when the amount of acid increases. Curves a, b, c, d and e correspond, respectively, to anilinium concentrations equal to 0, 1.8, 2.8, 4.0 and 5.2 mmol.L$^{-1}$. This is typical of electrocatalytic behavior in the production of dihydrogen.

Example 8

Illustration of Immobilization of Ligand 6 on ITO for Metal Complexation

-continued

The uncomplexed ligand 6 may be grafted onto an oxide according to a process similar to that given in Example 7. The material obtained can then complex a metal atom (copper, cobalt, nickel, etc.) present in a solution. The applications may concern the formation of an electrochemical metal scavenger if the substrate is conductive, materials for decontaminating effluents, etc.

The term "comprising one" should be understood as meaning "comprising at least one".

The invention claimed is:

1. Substrate, at the surface of which is immobilized at least one unit of formula (I):

(I)

in which:
$R_1$ and $R_2$, which may be identical or different, symbolize a group chosen from: —H, a halogen atom, a $C_1$ to $C_{20}$ ether, a linear or branched $C_1$ to $C_{20}$ alkyl chain, or a $C_5$ to $C_{30}$ aryl group,
X is a triazole ring product of a reaction of "click-chemistry" type and attached to the middle carbon of A,
Y is a spacer arm,
n is 0, and
A:
represents a saturated $C_3$ hydrocarbon-based chain.

2. Substrate according to claim 1, in which $R_1$ and $R_2$, which may be identical or different, symbolize a linear or branched $C_1$ to $C_{20}$ alkyl chain.

3. Substrate according to claim 2, in which $R_1$ and $R_2$, which may be identical or different, symbolize a linear or branched $C_1$ to $C_{20}$ alkyl chain interrupted with one or more heteroatoms and/or one or more aryl groups.

4. Substrate according to claim 1, in which $R_1$ and $R_2$, which may be identical or different, symbolize a $C_5$ to $C_{30}$ aryl group comprising one or more heteroatoms.

5. Substrate according to claim 1, in which $R_1$ and $R_2$, which may be identical or different, symbolize a group chosen from: a $C_1$ to $C_{20}$ ether, a linear or branched $C_1$ to $C_{20}$ alkyl chain, or a $C_5$ to $C_{30}$ aryl group, the said ether, the said alkyl chain and the said aryl group being substituted with at least one of the following groups: —OH, —NH$_2$, —NO$_2$, —COOH, —CONH$_2$, a triazole ring or —COOZ$_1$ with $Z_1$ representing a $C_1$ to $C_5$ alkyl group, a $C_1$ to $C_5$ alkoxy group or a halogen.

6. Substrate according to claim 1, in which X is of formula:

(IIA)

or (IIB)

in which:
* symbolizes a bond to A.

7. Substrate according to claim 6, in which X is of formula:

(IIB)

with * being as defined in claim 6.

8. Substrate according to claim 1, in which the unit of formula (I) has the following formula:

(IA)

in which $R_1$ and $R_2$ are as defined in claim 1 and X is as defined in claim 1.

9. Substrate according to claim 1, in which at least one unit of structure (I) is coordinated to at least one metal so as to form at least one metal complex (C).

10. Substrate according to claim 9, in which the metal is a transition metal of the Periodic Table.

11. Substrate according to claim 10, in which the metal is chosen from nickel (Ni) and cobalt (Co).

12. Substrate according to claim 9, in which the metal complex (C) formed with the said unit of formula (I) is as follows:

(C1)

( or (C2)

in which Z denotes a halogen atom and ** symbolizes the bond to X.

13. Substrate according to claim 1, in which the unit of formula (I) is bonded to the substrate via a linker arm.

14. Substrate according to claim 13, in which the linker arm is bonded to one or more units of formula (I).

15. Substrate according to claim 13, in which the linker arm is bonded to the substrate via a covalent or non-covalent interaction.

16. Substrate according to claim 1, characterized in that:
it is formed totally or partly from a material chosen from:
semiconductive oxides, or
conductive or semiconductive materials, or
it consists of one or more molecules of interest.

17. Substrate according to claim 16, characterized in that it is formed totally or partly from a material chosen from ITO (Indium Tin Oxide), single-wall or multi-wall carbon nanotubes or vitreous carbon.

18. Electrode comprising a substrate according to claim 1.

19. Electrolysis device comprising an electrode according to claim 18.

20. Ligand of formula (II):

(II)

in which:

$R_1$ and $R_2$, which may be identical or different, symbolize a group chosen from: —H, a halogen atom, a $C_1$ to $C_{20}$ ether, a linear or branched $C_1$ to $C_{20}$ alkyl chain, or a $C_5$ to $C_{30}$ aryl group, Y is a spacer arm,

N is 0, and

A:
represents a saturated $C_3$ hydrocarbon-based chain,

T symbolizes one of the following groups: $N_3$, $NH_2$ or $N=P(Ar)_3$ for which $(Ar)_3$ represents three identical or different $C_6$ to $C_{20}$ aromatic groups.

21. Ligand according to the preceding claim, in which T symbolizes $N=PPh_3$.

22. Ligand of formula (III):

(III)

in which:

$R_1$ and $R_2$, which may be identical or different, symbolize a group chosen from: —H, a halogen atom, a $C_1$ to $C_{20}$ ether, a linear or branched $C_1$ to $C_{20}$ alkyl chain, or a $C_5$ to $C_{30}$ aryl group, X is a triazole ring product of a reaction of "click-chemistry" type and attached to the middle carbon of A, Y is a spacer arm, N is 0, and A:
represents a saturated $C_3$ hydrocarbon-based chain, m is a number equal to 0 or 1, P symbolizes a $C_1$ to $C_{20}$ hydrocarbon-based chain, a $C_1$ to $C_{20}$ ether, a $C_1$ to $C_{20}$ ester or a $C_5$ to $C_{30}$ aryl group, and F denotes a reactive function that is capable of forming a covalent or non-covalent bond.

23. Ligand according to claim 22 in which:

$R_1$ and $R_2$, which may be identical or different, symbolize a linear or branched $C_1$ to $C_{20}$ alkyl chain, m=1, P symbolizes a $C_1$ to $C_{20}$ ether, and F is COON.

* * * * *